(12) United States Patent
Palushi et al.

(10) Patent No.: US 11,324,634 B2
(45) Date of Patent: May 10, 2022

(54) PLUG WITH ISTHMUS ANCHOR FOR TREATING PATULOUS EUSTACHIAN TUBE

(71) Applicants: Acclarent, Inc., Irvine, CA (US); The Children's Medical Center Corporation, Boston, MA (US)

(72) Inventors: Jetmir Palushi, Irvine, CA (US); Henry F. Salazar, Pico Rivera, CA (US); Jeffrey B. Everett, Easton, PA (US); Heather M. Wozniak, Oro Valley, AZ (US); Dennis S. Poe, Chestnut Hill, MA (US)

(73) Assignees: Acclarent, Inc., Irvine, CA (US); The Children's Medical Center Corporation, Boston, MA (US)

( * ) Notice: Subject to any disclaimer, the term of this patent is extended or adjusted under 35 U.S.C. 154(b) by 266 days.

(21) Appl. No.: 16/513,967

(22) Filed: Jul. 17, 2019

(65) Prior Publication Data
US 2020/0069473 A1 Mar. 5, 2020

Related U.S. Application Data

(60) Provisional application No. 62/727,165, filed on Sep. 5, 2018.

(51) Int. Cl.
*A61F 11/00* (2006.01)
*A61B 17/24* (2006.01)

(52) U.S. Cl.
CPC ............. *A61F 11/002* (2013.01); *A61B 17/24* (2013.01); *A61F 11/004* (2013.01); *A61M 2210/0675* (2013.01)

(58) Field of Classification Search
CPC .............................. A61F 11/002; A61F 11/08; A61F 2002/8483; A61F 11/045; A61F 2011/085; A61B 17/24; A61M 2210/0675
See application file for complete search history.

(56) References Cited

U.S. PATENT DOCUMENTS

| | | | | |
|---|---|---|---|---|
| 2,487,038 A | * | 11/1949 | Baum | A61F 11/08 181/135 |
| 4,353,364 A | * | 10/1982 | Woods | A61F 11/08 128/867 |
| 2008/0183280 A1 | * | 7/2008 | Agnew | A61F 2/2418 623/1.24 |

(Continued)

FOREIGN PATENT DOCUMENTS

WO   WO 2016/160808 A1   10/2016

OTHER PUBLICATIONS

International Search Report and Written Opinion dated Nov. 22, 2019 for Application No. PCT/IB2019/057478, 17 pgs.

(Continued)

*Primary Examiner* — Nathan R Price
*Assistant Examiner* — Justin L Zamory
(74) *Attorney, Agent, or Firm* — Frost Brown Todd LLC

(57) ABSTRACT

A plug is configured to maintain position within a Eustachian tube of a patient. The plug includes a proximal portion and a distal portion. The proximal portion includes a first body dimensioned bear radially outwardly against the Eustachian tube of the patient. The distal portion includes an anchoring assembly that is configured to lock the plug in the Eustachian tube of the patient. The plug may be formed of a bioabsorbable material.

18 Claims, 7 Drawing Sheets

(56) References Cited

U.S. PATENT DOCUMENTS

| | | | |
|---|---|---|---|
| 2008/0319424 A1* | 12/2008 | Muni | A61B 34/20 |
| | | | 604/890.1 |
| 2010/0174366 A1* | 7/2010 | Avior | A61F 11/002 |
| | | | 623/10 |
| 2010/0274188 A1 | 10/2010 | Chang et al. | |
| 2013/0274715 A1 | 10/2013 | Chan et al. | |
| 2015/0202089 A1 | 7/2015 | Campbell et al. | |
| 2015/0374963 A1 | 12/2015 | Chan et al. | |
| 2016/0287445 A1* | 10/2016 | Wasicek | A61M 25/10184 |

OTHER PUBLICATIONS

Ikeda, Ryoukichi, Toshiaki Kikuchi, and Toshimitsu Kobayashi. "Endoscope-assisted silicone plug insertion for patulous Eustachian tube patients." The Laryngoscope 127.9 (2017): 2149-2151.

Ikeda, Ryoukichi, et al. "Efficacy of a silicone plug for patulous eustachian tube: A prospective, multicenter case series." The Laryngoscope (2019).

* cited by examiner

PLUG WITH ISTHMUS ANCHOR FOR TREATING PATULOUS EUSTACHIAN TUBE

PRIORITY

This application claims priority to U.S. Provisional Pat. App. No. 62/727,165, entitled "Plug with Isthmus Anchor for Treating Patulous Eustachian Tube," filed Sep. 5, 2018, the disclosure of which is incorporated by reference herein.

BACKGROUND

Referring to FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. A narrowed region known as the isthmus (29) of the ET (26) provides a transition between the remainder of the ET (26) and the middle ear (14). The isthmus (29) is the narrowest part of the ET (26) at the junction of the bony and cartilaginous parts of the ET (26) (i.e., where the bony canal meets the cartilaginous tube). The isthmus (29) thus has a reduced inner diameter compared to the remaining portion of the ET (26) that extends between the isthmus (29) and the pharyngeal ostium (28); and provides a density that is substantially greater than the density of the tissue of the remaining portion of the ET (26) that extends between the isthmus (29) and the pharyngeal ostium (28).

The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This may occur frequently in children in connection with an upper respiratory infection and account for hearing impairment associated with this condition.

When the ET (26) is blocked, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Finally, the fluid can become infected, which can lead to pain, illness, and temporary hearing loss. If the inner ear (14) is affected, the patient may feel a spinning or turning sensation (vertigo).

Methods for treating the middle ear (14) and restriction or blockage of the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pub. No. 2015/0374963, entitled "Vent Cap for a Eustachian Tube Dilation System," published Dec. 31, 2015, issued as U.S. Pat. No. 10,350,396 on Jul. 16, 2019, the disclosure of which is incorporated by reference herein.

In some cases, rather than being restricted or blocked, the ET (26) may fail to close properly, or such that the ET (26) takes an inordinately prolonged amount of time to close after being opened, such that the ET (26) substantially remains in a patulous state. This may adversely affect a patient by causing variations in the upper airway pressure around the ET (26) and the middle ear (14). In some patients, a patulous ET (26) may create a feeling of dry sinus, an increased breathing rate with physical activity, higher than usual perceived volumes of sound, and/or other undesirable consequences. It may therefore be desirable to provide a form of treatment for a patulous ET (26). It may further be desirable for such a treatment to still provide some degree of ventilation and drainage for the ET (26), without completely closing the ET (26).

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
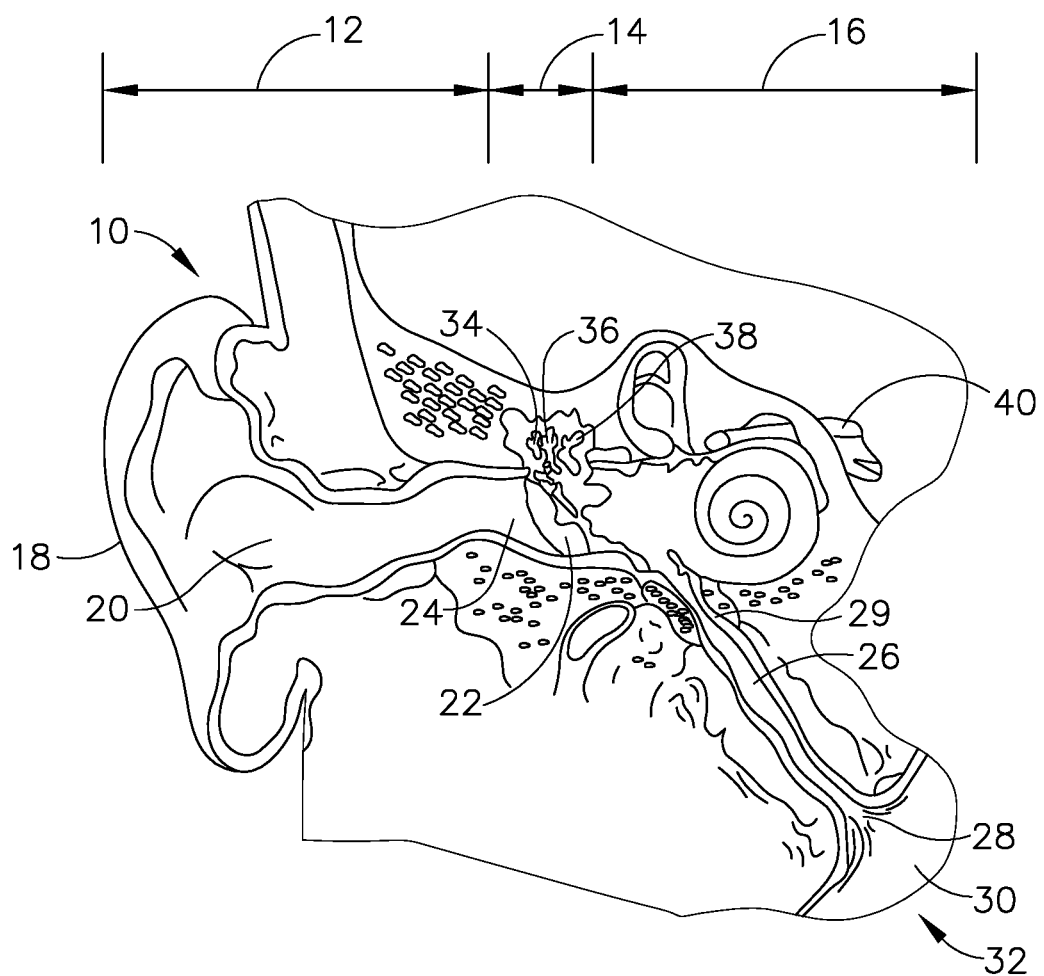
FIG. 1 depicts a cross-sectional view of a human ear showing the inner, middle and outer ear portions and the Eustachian tube connecting the middle ear with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Implants and Methods of Treating the Eustachian Tube

As noted above, some patients may have an ET (26) that remains patulous for a prolonged period, which may be undesirable for various reasons. In some instances, if a patulous ET (26) is maintained in a radially outwardly stressed state (as comparted to ET (26) in the patulous state) for a prolonged period of time (e.g. nine to twelve months), the prolonged stress may trigger a process were cells within ET (26) regenerate such that ET (26) transitions from the undesirable patulous state toward a more desirable, normal functioning state. For instance, imposing a radially outward stress on the ET (26) may generate scar tissue in the ET (26). It may therefore be desirable to insert an implant or other device into a patulous ET (26) of a patient, where the inserted implant or other device is capable of bearing radially outwardly against the sidewall of a patulous ET (26) for a prolonged period of time. It may also be desirable to have an implant or other device that is sufficiently flexible to conform to the anatomy shape of a patulous ET (26), or various other anatomical passageways, after or during deployment. Further, it may be desirable to have an implant or other device that is made of bioabsorbable materials configured to bio-absorb after a desired prolonged period of time, such that there is no need for removal of the implant or other device after deployment.

The following description provides various examples of devices and implants that may be deployed within the ET (26) to bear outwardly against the inner diameter of the ET (26) for a prolonged period of time. Such devices may treat a dysfunctional ET (26), repair a patulous ET (26), occlude a leaking ET (26) (e.g., a cerebrospinal fluid leak, etc.), treat a chronic ear disease, or provide other results. Other suitable ways in which the below-described implants and/or devices may be used will be apparent to those of ordinary skill in the art in view of the teachings herein.

Figure 2:
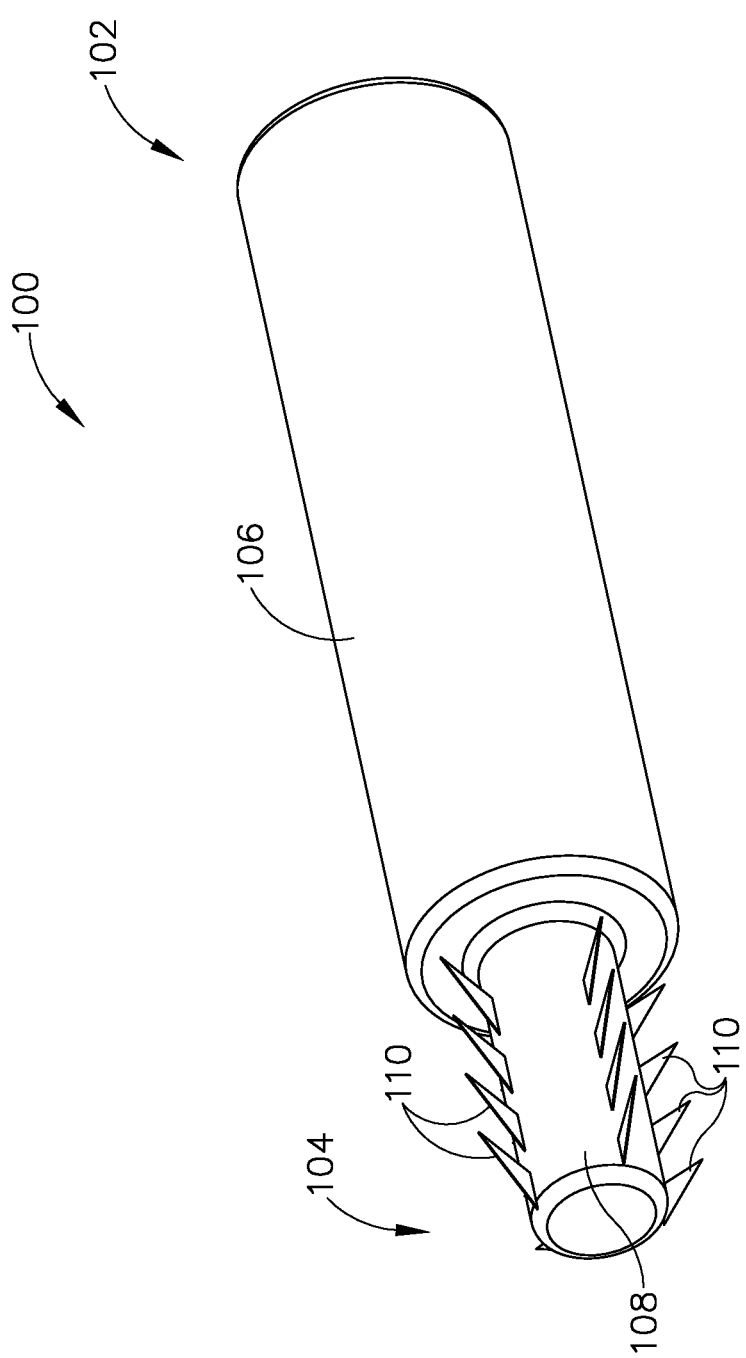
FIG. 2 depicts a perspective view of an exemplary plug.
Figure 3:
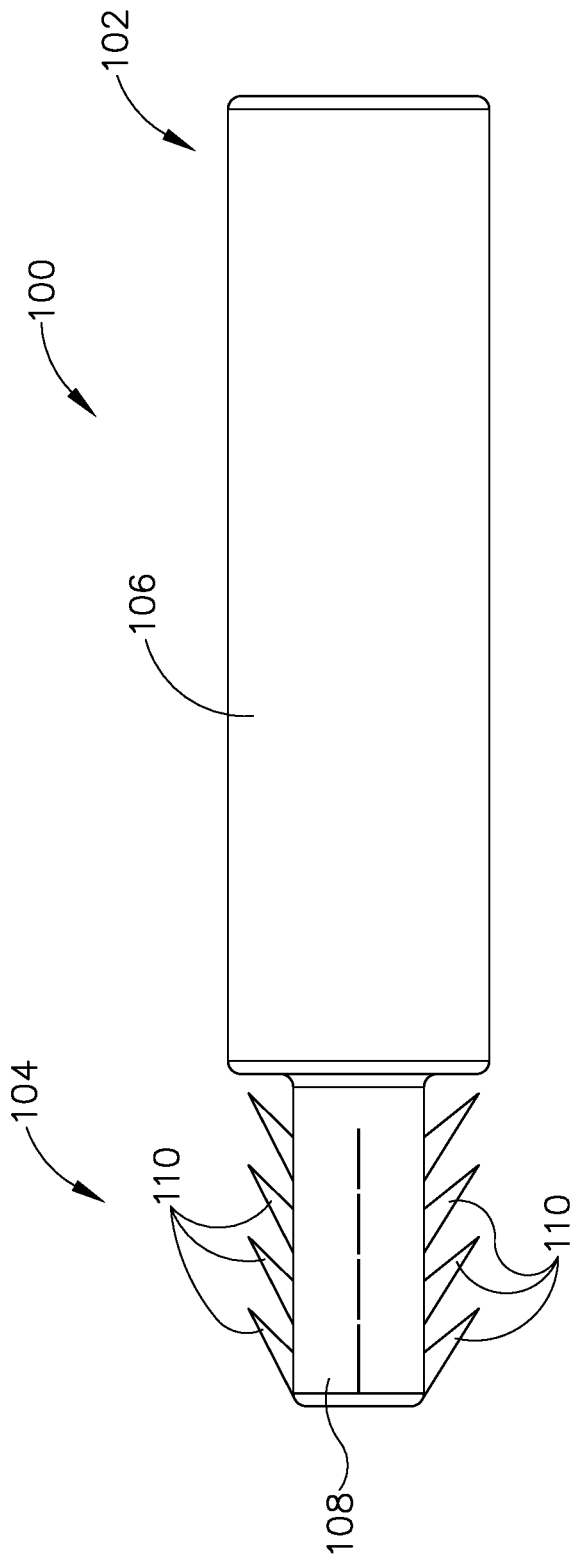
FIG. 3 depicts a side elevational view of the plug of FIG. 2.
Figure 4:
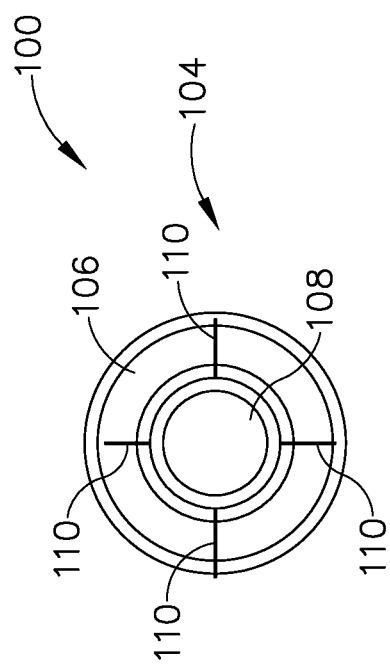
FIG. 4 depicts a front elevational view of the plug of FIG. 2.

FIG. 2 shows an exemplary plug (100) that may be deployed within ET (26). While the term "plug" is used herein, that term should not be read as necessarily requiring the plug to completely block fluid communication through the ET (26) (though some version of plug (100) may in fact block fluid communication through the ET (26)). For instance, some versions of plug (100) may operate like a shim. Thus, the term "plug" should be read broadly to include structures like shims. Plug (100) extends along a longitudinal profile from a proximal portion (102) to a distal portion (104). As will be described in greater detail below, proximal portion (102) is dimensioned to slightly expand or stretch ET (26) of the patient when plug (100) is suitably deployed. As will also be described in greater detail below, distal portion (104) is dimensioned to be inserted within isthmus (29) and is configured to attach to isthmus (29) of the patient to help promote stability of a deployed plug (100) within ET (26).

Figure 5A:
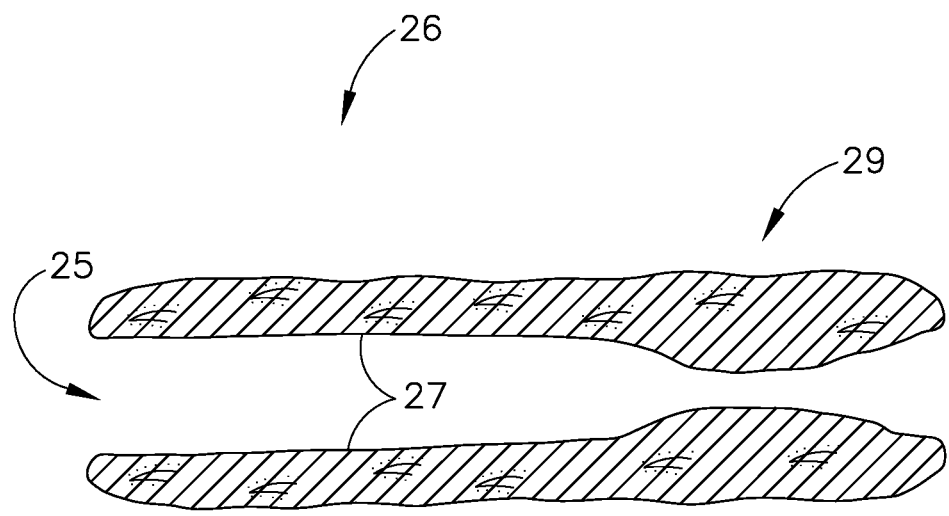
FIG. 5A depicts a cross-sectional view of a patulous Eustachian tube of a patient.
Figure 5B:
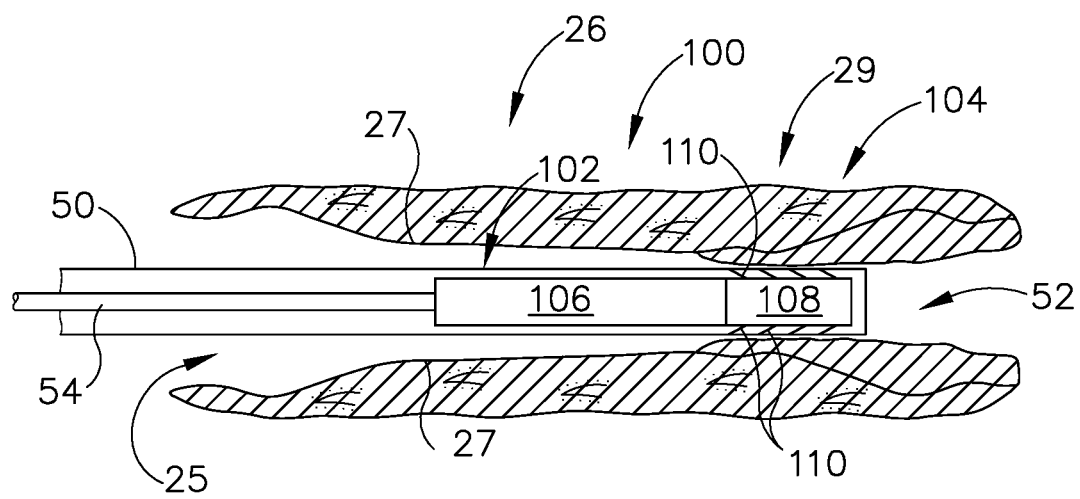
FIG. 5B depicts a cross-sectional view of the Eustachian tube of FIG. 5A, with a sheath slidably advanced therein, the sheath containing the plug of FIG. 2 therein, with the plug restricted to a contracted state by the sheath.
Figure 5C:
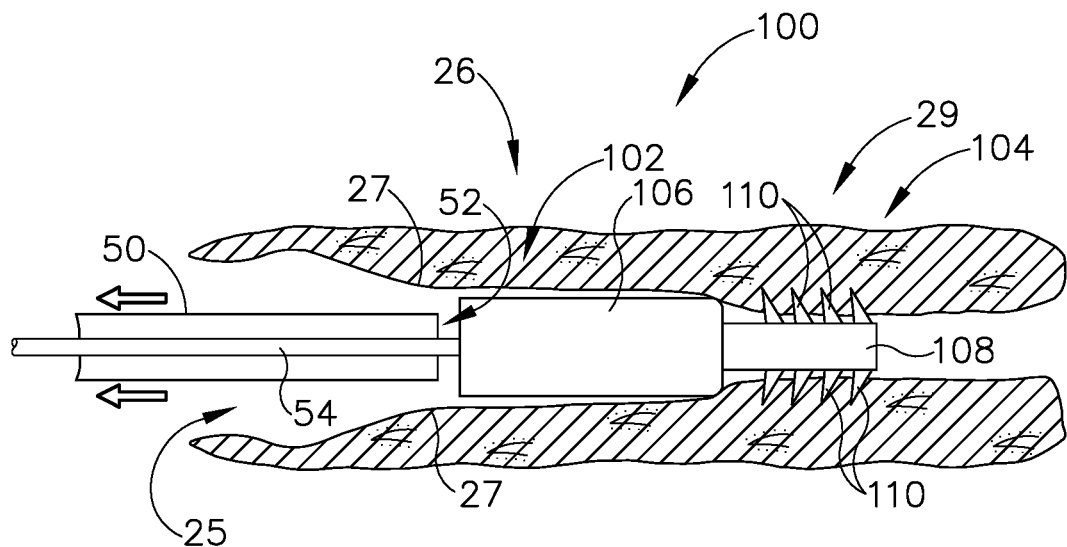
FIG. 5C depicts a cross-sectional view of the Eustachian tube of FIG. 5A, where the sheath of FIG. 5B is partially removed such that the plug of FIG. 2 inserted within the Eustachian tube in an expanded state, thereby bearing against the side walls of the Eustachian tube.

Proximal portion (102) includes a first body (106). First body (106) is a longitudinal, cylindraceous body that is configured to be compressible. As seen in FIG. 2, first body (106) is configured to naturally be in an expanded or enlarged state by default. First body (106) is formed of a bioabsorbable, elastomeric material that has elastic properties allowing first body (106) to be compressible between the expanded state and a compressed state, as seen in FIG. 5B. In other words, first body (106) is configured to be radially compressed and axially lengthened when compressed from the original expanded state to the compressed state. For instance, first body (106) may be operable to radially compress and axially stretch to a smaller profile upon the application of a predetermined force onto the exterior surface of first body (106), thereby transitioning first body (106) from the expanded state into the compressed state. Some variations of first body (106) are non-compressible.

When plug (100) is suitably deployed, first body (106) is dimensioned to abut against an interior wall (27) of ET (26) such that first body (106) bears against ET (26). In some scenarios, first body (106) slightly stretches ET (26). First body (106) may have any suitable dimension, while in the expanded state, as would be apparent to one skilled in the art in view of the teachings herein. For instance, first body (106) may have a diameter ranging between about 5 millimeters to about 9 millimeters. Additionally, first body (106) may have a varying radial dimension along the longitudinal profile of first body (106). For instance, first body (106) may have a longitudinal profile where the proximal end of first body (106) is larger than the portion of first body (106) connected to distal portion (104). As another mere example, first body (106) may have a longitudinal profile with an undulating surface. Additionally, the geometrical shape of first body (106) may have any suitably shape that would be apparent to one skilled in the art in view of the teachings herein. As yet another merely illustrative example, first body (106) may define one or more longitudinal ventilation channels that enable fluid communication between pharyngeal ostium (28) and isthmus (29), thereby providing a ventilation pathway between the middle ear (14) and the nasopharynx (30).

First body (106) may be in the compressed state while contained within a sheath (50) during deployment of plug (100). First body (106) may then naturally return to the expanded state when no longer contained within sheath (50). As will be described in greater detail below, containing first body (106) within sheath (50) during deployment of plug (100) may allow first body (106) to be initially inserted within the desired location of ET (26) without causing unnecessary discomfort for the patient. While first body (106) is sufficiently resilient to transition between the naturally expanded state and the compressed state, first body (106) may also be sufficiently resilient such that when deployed within ET (26), first body (106) maintains sufficient contact with interior wall (27) to suitably bear outwardly against ET (26). In other words, first body (106) is sufficiently flexible to transition into the compressed state within the confines of sheath (50), but also sufficiently resilient to bear outwardly against interior walls (27) of ET (26) while in the expanded state.

While the longitudinal profile of proximal portion (102) is shown with first body (106) in a linear arrangement, first body (106) may flex to form other suitable longitudinal profiles, such as an S-shaped arrangement. Therefore, when plug (100) is suitably deployed with ET (26), first body (106) may contact interior wall (27) of ET (26) in such a manner that first body (106) defines a longitudinal profile similar to the longitudinal profile of ET (26). The flexible longitudinal profile may help reduce pain and or discomfort experienced by the patient during or after plug (100) has been deployed within ET (26).

First body (106) is made from a bioabsorbable material configured to completely absorb after deployment of plug (100) after any suitable period of time that would be apparent to one skilled in the art in view of the teachings herein. As one example, first body (106) may be formed from a material configured to completely absorb after about nine to twelve months.

Distal portion (104) includes a second body (108) and a plurality of barbs (110), both of which may be made out of any suitable bioabsorbable material as would be apparent to one skilled in the art in view of the teachings herein. For instance, second body (108) and barbs (110) may be made of the same bioabsorbable material as first body (106). Alternatively, second body (108) and barbs (110) may be made of a bioabsorbable material configured to bio-absorb within ET (26) after a longer or shorter period of time as compared to first body (106). Second body (108) and barbs (110) may be made out of a different bioabsorbable material as well.

Second body (108) extends distally from first body (106). Second body (108) is dimensioned for insertion within isthmus (29) of patient when plug (100) is deployed. Second body (108) may be compressible, similar to first body (106). Alternatively, second body (108) may be non-compressible. Barbs (110) are connected to and extend outwardly away from second body (108). Barbs (110) also extend proximally at angles that are oblique to the longitudinal axis of plug (100). In the current example, barbs (110) are disposed about second body (108) in multiple linear arrays disposed circumferentially about second body (108). However, barbs (110) may be disposed about second body (108) in any suitable arrangement as would be apparent to one skilled in the art in view of the teachings herein. Barbs (110) are configured to anchor to isthmus (29) when deployed such that plug (100) is secured within ET (26).

Barbs (110) are resiliently flexible to transition between a natural expanded state (as shown in FIGS. 2-4 and 5C-5D) and a compressed state (as shown in FIG. 5B). In particular, barbs (110) may be contained within a sheath (50) in the compressed state during deployment of plug (100), and then naturally return to the expanded state when barbs (110) are no longer contained within sheath (50). Barbs (110) may be configured to anchor to isthmus (29) by penetrating portions of isthmus (29). Alternatively, barbs (110) may be configured anchor to isthmus (29) via any other suitable means as would be apparent to one skilled in the art in view of the teachings herein. For instance, barbs (110) may be configured to abut against interior wall of isthmus (29) with sufficient frictional forces to anchor plug (100).

The entirety of plug (100), or selected portions of plug (100), may be coated or otherwise implemented with any suitable drug or therapeutic agent as would be apparent to one skilled in the art in view of the teachings herein. For example, first body (106) may be coated with a therapeutic agent. As another mere example, barbs (110) may be coated with a therapeutic agent. In versions incorporating a therapeutic agent, the therapeutic agent may be configured for immediate release. Alternatively, the therapeutic agent may be configured for delayed release. Alternatively still, the therapeutic agent may be configured for sustained delivery over a certain period of time. Some versions may include more than one therapeutic agent, with the different therapeutic agents having different release times or release rates.

FIGS. 5A-45E show an exemplary deployment and use of plug (100) with a patulous ET (26). FIG. 5A shows ET (26) in a patulous state. First, as shown in FIG. 5B, an operator may advance a deployment mechanism containing plug (100) transnasally or transorally into ET (26) via the pharyngeal ostium (28). In the present example, deployment mechanism includes a sliding sheath (50) comprising an open distal end (52), and a push rod (54) located within the confines of sliding sheath (50). Plug (100) is constrained within sliding sheath (50). Sliding sheath (50) is advanced within channel (25) of ET (26) until second body (108) is located directly adjacent to isthmus (29) as shown in FIG. 5B. Any suitable deployment mechanism may be used as would be apparent to one skilled in the art in view of the teachings herein.

Plug (100) is housed within sliding sheath (50) such that second body (108) is located proximal to open distal end (52) of sliding sheath (50), and such that barbs (110) are in the compressed state within sliding sheath (50). In some other variations, the inner diameter of sheath (50) is sized such that barbs (110) are not compressed within sliding sheath (50), even though barbs (110) are fully contained within sliding sheath (50). First body (106) is confined in the compressed state within sliding sheath (50). A distal end of push rod (54) may be adjacent to the proximal end of first body (106) when sliding sheath (50) is advanced into ET (26). When plug (100) is positioned within ET (26) at the desired location, the operator may utilize deployment mechanism to suitably deploy plug (100) within ET (26). In the current example, and shown between FIGS. 5B-5D, the operator may slide sheath (50) proximally while push rod (54) remains stationary in contact with the proximal end of first body (106). Push rod (54) therefore keeps plug (100) longitudinally stationary within ET (26) while sheath (50) is retracted proximally relative to ET (26). Alternatively, the operator may actuate push rod (54) distally while keeping sheath (50) stationary, therefore distally advancing plug (100) out of open distal end (52) of sheath (50).

Figure 5D:
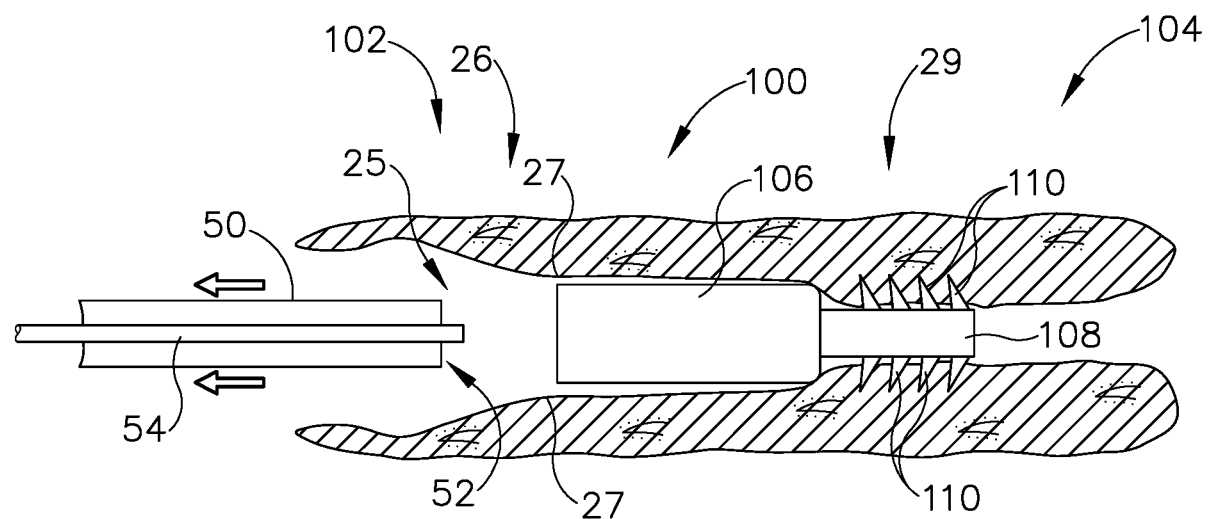
FIG. 5D depicts a cross-sectional view of the Eustachian tube of FIG. 5A, where the sheath of FIG. 5B is removed, and the plug of FIG. 2 is inserted within the Eustachian tube in the expanded state, thereby bearing against the side walls of the Eustachian tube.
Figure 5E:
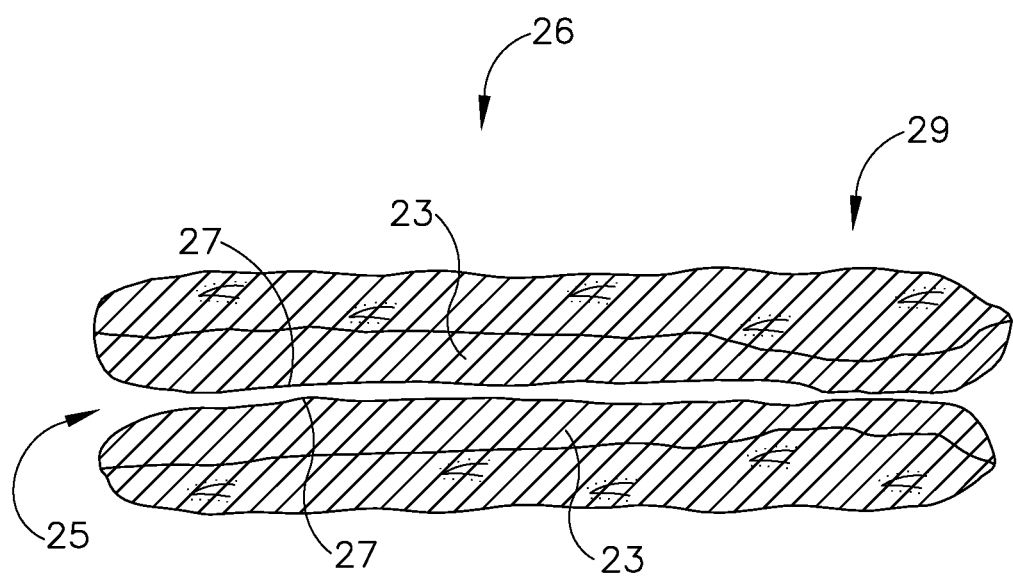
FIG. 5E depicts a cross-sectional view of the Eustachian tube of FIG. 5A, with the Eustachian tube in a normally functioning state after the plug of FIG. 2 has been bio-absorbed, where the Eustachian tube has regenerated cell growth.

Either way, when plug (100) is deployed, as shown in FIG. 5D, distal barbs (110) and first body (106) are no longer constrained in the compressed position such that barbs (110) and first body (106) resiliently return to the natural expanded position. In the current example, with barbs (110) in the natural expanded position, barbs (110) penetrate isthmus (29) to help initially anchor plug (100) within ET (26). As mentioned above, first body (106) bears outwardly against interior wall (27) of ET (26) while first body (106) is in the natural expanded position. In some cases, first body (106) increases the inner diameter defined by interior wall (27) by stretching or compressing the tissue of interior wall (27). The radial stress imposed by first body (106) on interior wall (27) causes the generation of additional tissue (23) in the ET (26). After a suitable period of time, as shown in FIG. 5E, plug (100) is bio-absorbed into adjacent anatomy. The additional tissue (23) remains in the ET (26), thereby providing ET (26) in a non-patulous state. In other words, the additional tissue (23) generated in response to stress imposed by first body (106) results in ET (26) in a normal functioning state.

While plug (100) of the present example includes two bodies (106, 108), with barbs (110) being positioned only along second body (108), this configuration may be modified if desired. By way of example only, a variation of plug (100) may be formed like second body (108) along the entire length of the plug, such that the outer diameter is consistent along the entire length of the plug; and such that barbs (110) are positioned along the entire length of the plug. In some such version, plug (100) is formed like a barbed suture. As yet another merely illustrative variation, the plug still includes two bodies (106, 108), yet barbs (110) are positioned along both bodies (106, 108). Other variations will be apparent to those skilled in the art in view of the teachings herein.

While plug (100) is described above as being formed of a bioabsorbable material, some other variations, may be formed of a non-bioabsorbable material. Thus, plug (100) need not necessarily be formed of bioabsorbable material in all cases. Regardless of whether plug (100) is bioabsorbable or non-bioabsorbable, plug (100) may include various kinds of expandable structures including but not limited to mesh, barbs (100), flanges, porous materials, compressible materials, or various other structures as will be apparent to those skilled in the art in view of the teachings herein.

Some variations of plug (100) may include a distal portion that protrudes into the middle ear (14) of the patient. Such a distal portion may be configured to anchor the rest of plug (100) in the ET (26), such that plug (100) need not necessarily include barbs (110) that are configured and positioned to anchor to the isthmus (29). In addition, or in the alternative, some variations of plug (100) may include a proximal portion that protrudes into the nasopharynx region (30) of the throat (32). Such a proximal portion may be configured to anchor the rest of plug (100) in the ET (26) by anchoring to the nasopharyngeal orifice of the ET (26), such that plug (100) need not necessarily include barbs (110) that are configured and positioned to anchor to the isthmus (29).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A plug configured to maintain position within a Eustachian tube of a patient, the plug comprising: (a) a proximal portion, the proximal portion comprising a first body dimensioned bear radially outwardly against the Eustachian tube of the patient; and (b) a distal portion comprising an anchoring assembly, wherein the anchoring assembly is configured to lock the plug in the Eustachian tube of the patient.

Example 2

The plug of Example 1, wherein the first body comprises a compressible material configured to transition between a naturally expanded state and a constrained state.

Example 3

The plug of any one or more of Examples 1 through 2, wherein the plug is at least partially coated with a therapeutic agent.

Example 4

The plug of Example 3, wherein the proximal portion is coated with the therapeutic agent.

Example 5

The plug of any one or more of Examples 3 through 4, where the distal portion of coated with the therapeutic agent.

Example 6

The plug of any one or more of Examples 1 through 5, wherein the distal portion comprises a second body extending distally from the first body.

Example 7

The plug of Example 6, wherein the second body comprises a compressible material.

Example 8

The plug any one or more of Examples 6 through 7, wherein the anchoring assembly comprises a plurality of barbs extending from the second body.

Example 9

The plug of Example 8, wherein the plurality of barbs are resiliently coupled to the second body.

Example 10

The plug of any one or more of Examples 8 through 9, wherein the plurality of barbs further comprises an annular array of barbs.

Example 11

The plug of any one or more of Examples 8 through 10, wherein the plurality of barbs further comprises a linear array of barbs.

Example 12

The plug of any one or more of Examples 1 through 11, wherein the first body is configured to partially flex to change a longitudinal profile of the first body.

Example 13

The plug of any one or more of Examples 1 through 12, wherein the first body and the distal portion are formed of a bioabsorbable material.

Example 14

The plug of any one or more of Examples 1 through 13, wherein plug is formed of a bioabsorbable material that is configured to bio-absorb after being deployed in the Eustachian tube for nine to twelve months.

Example 15

The plug of any one or more of Examples 1 through 14, further comprising a sheath configured to maintain the first body in a radially compressed state.

Example 16

A plug configured to bear radially outwardly against a Eustachian tube of a patient, the plug comprising: (a) a compressible first body configured to transition between a compressed state and a naturally expanded state, wherein the first body is dimensioned to bear radially outwardly against the Eustachian tube of the patient in the naturally expanded state; and (b) an anchoring assembly, wherein the anchoring assembly is configured to lock the plug in the Eustachian tube of the patient by engaging a structure in the middle ear, a structure in the Eustachian tube, or the nasopharyngeal orifice of the Eustachian tube.

Example 17

The plug of claim 16, wherein the anchoring assembly comprises a plurality of barbs.

Example 18

The plug of Example 17, wherein the barbs are configured to penetrate an isthmus of the Eustachian tube.

Example 19

A plug configured to maintain position in a Eustachian tube of a patient, the plug comprising: (a) a proximal portion, the proximal portion comprising a first body dimensioned fit in the Eustachian tube of the patient; and (b) a distal portion comprising an anchoring assembly, wherein the anchoring assembly is configured to lock the plug in the Eustachian tube of the patient, wherein the anchoring assembly comprises a second body extending from the first body and a plurality of barbs attached to the second body.

Example 20

The plug of Example 19, wherein the barbs are arranged in multiple annular arrays about the second body.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A plug configured to maintain position within a Eustachian tube of a patient, the plug comprising:
    (a) a proximal portion, the proximal portion comprising a first body comprising an engagement surface dimensioned to bear radially outwardly against the Eustachian tube of the patient, wherein the first body comprises a distally presented face defined by a portion of the engagement surface; and
    (b) a distal portion comprising a second body extending distally from the distally presented face of the first body and an anchoring assembly, wherein the anchoring assembly is configured to lock the plug in the Eustachian tube of the patient, wherein the anchoring assembly comprises a plurality of barbs extending from the second body.

2. The plug of claim 1, wherein the first body comprises a compressible material configured to transition between a naturally expanded state and a constrained state.

3. The plug of claim 1, wherein the plug is at least partially coated with a therapeutic agent.

4. The plug of claim 3, wherein the proximal portion is coated with the therapeutic agent.

5. The plug of claim 3, wherein the distal portion is coated with the therapeutic agent.

6. The plug of claim 1, wherein the second body comprises a compressible material.

7. The plug of claim 1, wherein the anchoring assembly comprises a plurality of barbs extending from the second body.

8. The plug of claim 7, wherein the plurality of barbs are resiliently coupled to the second body.

9. The plug of claim 7, wherein the plurality of barbs further comprises an annular array of barbs.

10. The plug of claim 7, wherein the plurality of barbs further comprises a linear array of barbs.

11. The plug of claim 1, wherein the first body is configured to partially flex to change a longitudinal profile of the first body.

12. The plug of claim 1, wherein the first body and the distal portion are formed of a bioabsorbable material.

13. The plug of claim 1, wherein plug is formed of a bioabsorbable material that is configured to bio-absorb after being deployed in the Eustachian tube for nine to twelve months.

14. The plug of claim 1, further comprising a sheath configured to maintain the first body in a radially compressed state.

15. A plug configured to bear radially outwardly against a Eustachian tube of a patient, the plug comprising:
    (a) a compressible first body configured to transition between a compressed state and a naturally expanded state, wherein the first body comprises an engagement surface dimensioned to bear radially outwardly against the Eustachian tube of the patient in the naturally expanded state, wherein the first body comprises a distally facing surface defined by a distal end of the engagement surface; and
    (b) an anchoring assembly comprising a second body and a plurality of barbs, wherein the second body extends from the distally facing surface of the first body, wherein the plurality or barbs extend radially from the second body in a direction toward the distally facing surface of the first body, wherein the anchoring assembly is configured to lock the plug in the Eustachian tube of the patient by engaging a structure in the middle ear, a structure in the Eustachian tube, or the nasopharyngeal orifice of the Eustachian tube.

16. The plug of claim 15, wherein the barbs are configured to penetrate an isthmus of the Eustachian tube.

17. A plug configured to maintain position in a Eustachian tube of a patient, the plug comprising:
    (a) a proximal portion, the proximal portion comprising a first body, wherein the first body comprises an exterior surface and a distally facing surface, wherein the exterior surface is dimensioned abut against the Eustachian tube of the patient, wherein the distally facing surface is defined by the exterior surface; and
    (b) a distal portion comprising an anchoring assembly comprising a second body and a plurality of barbs extending from the second body toward the distally facing surface, wherein the second body extends distally from the distally facing surface of the first body, wherein the anchoring assembly is configured to lock the plug in the Eustachian tube of the patient, wherein the anchoring assembly comprises a second body extending from the first body and a plurality of barbs attached to the second body.

18. The plug of claim 17, wherein the barbs are arranged in multiple annular arrays about the second body.

* * * * *